US008178113B2

(12) United States Patent
Abdullah

(10) Patent No.: US 8,178,113 B2
(45) Date of Patent: May 15, 2012

(54) COSMETIC COMPOSITION AND METHODS OF USE

(76) Inventor: Sheikh Ahmed Abdullah, Fargo, ND (US)

( * ) Notice: Subject to any disclaimer, the term of this patent is extended or adjusted under 35 U.S.C. 154(b) by 0 days.

(21) Appl. No.: 11/695,387

(22) Filed: Apr. 2, 2007

(65) Prior Publication Data

US 2008/0241291 A1  Oct. 2, 2008

(51) Int. Cl.
*A61K 8/02* (2006.01)
*A61K 31/19* (2006.01)
*A01N 65/00* (2009.01)
*A01N 37/00* (2006.01)

(52) U.S. Cl. .................. 424/401; 424/744; 514/557
(58) Field of Classification Search .................. 424/401, 424/744
See application file for complete search history.

(56) References Cited

U.S. PATENT DOCUMENTS

| | | | |
|---|---|---|---|
| 5,444,091 A | 8/1995 | Rapaport et al. | |
| 5,607,980 A | 3/1997 | McAtee et al. | |
| 5,612,324 A | 3/1997 | Guang Lin et al. | |
| 5,652,228 A | 7/1997 | Bissett | |
| 5,681,852 A | 10/1997 | Bissett | |
| 5,760,079 A | 6/1998 | Shaffer et al. | |
| 5,811,413 A | 9/1998 | Blank et al. | |
| 5,814,662 A | 9/1998 | Znaiden et al. | |
| 5,883,085 A | 3/1999 | Blank et al. | |
| 5,945,409 A | 8/1999 | Crandall | |
| 6,071,541 A * | 6/2000 | Murad | 424/616 |
| 6,150,403 A * | 11/2000 | Biedermann et al. | 514/460 |
| 6,403,108 B1 * | 6/2002 | Abdullah | 424/401 |

OTHER PUBLICATIONS

Grimes et al.; "The Use of Polyhydroxy Acids (PHAs) in Photaged Skin;" Cutis. 2004; 73(suppl 2):3-13.
Edison et al.; "A Polyhydroxy Acid Skin Care Regimen Provides Antiaging Effects Comparable to an Alpha-Hydroxyacid Regimen;" Cutis. 2004; 73(suppl 2):14-17.
The Beauty of Understating and Over Delivering; http://www/lexlienterprises.com/2/Footer/LW_Vision.cfm; A.V.E. International, Inc.; 1 page; printed Jul. 7, 2006.
http://nettrax3.infotraxsys.com/lexli/ShoppingCart/Shop.cfm?CurrPage+FrontPage&Next....; A.V.E. International, Inc.; 6 pages; printed Jul. 7, 2006.
http://www.ave.cc/Lisa/ReadStory.cfm; A.V.E. International, Inc.; 2 pages; pinrted Jul. 23, 2006.
Exfoliate Your Fine lines and Wrinkles Away!; http://www.ave.cc/2/AVE21/AVEIntro.cfm; A.V.E. International, Inc.; 2 pages; printed Nov. 15, 2006.
AVE: Real Science, Real Results; http://www.ave.cc/2/JustTheFacts/AVEIntro.cfm; A.V.E. International, Inc.; 4 pages; printed Nov. 15, 2006.
Down to Basics: AVE's 4 Step Skin Care Plan; http://www.ave.cc/2/JustTheFacts/4StepProgram.cfm; A.V.E. International, Inc.; 2 pages; printed Nov. 15, 2006.
The Importance of Exfoliation and Efficacy of AVE 2.1; http://www.ave.cc/2/AVE21/AVEScience.cfm; A.V.E. International, Inc.; 6 pages; printed Nov. 15, 2006.
Ascorbyl Palmitate; http://www.pdrhealth.com/drug_info/nmdrugprofiles/nutsupdrugs/asc_0334.shtml; 2 pages; printed Jul. 24, 2006.
Ascorbyl Palmitate; http://www.lef.org.newshop/items/item00082.html; 2 pages; printed Jul. 24, 2006.
The Bioavailability of Different Forms of Vitamin C (Ascorbic Acid); http://www.lpi.oregonstate.edu/infocenter/vitamins/vitaminC/vitCform.html; 5 pages; pring Jul. 24, 2006.
File://C:\IE_Temp\OLKB\ave_sc_page1.htm; A.V.E. International, Inc; 2 pages; printed Jul. 20, 2006.
File://C:\IE_Temp\OLKB\ave_sc_page2.htm; A.V.E. International, Inc; 2 pages; printed Jul. 20, 2006.
AVE 2.1 is Skin Rejuvenation; File://C:\IE_Temp\OLKB\ave21_page_1.htm; A.V.E. International, Inc; 2 pages; printed Jul. 20, 2006.
What is Exfoliation?; File://C:\IE_Temp\OLKB\ave21_page_2.htm; A.V.E. International, Inc; 5 pages; printed Jul. 20, 2006.
The Beauty of Building an AVE Business; http://www.ave.cc/2/Why_LEXLI/Top_Reasons.cfm; A.V.E. International, Inc.; 2 pages; Sep. 7, 2006.
Skin Care Products, Cosmetics, Symantic; LexLi Skin Care Quarterly; Ahmed Abdullah, M.D.; Winter/Spring 2001; 4 pages.
Four Steps to Healthy Sking; The LexLi Communique; Ahmed Abdullah, M.D., F.A.C.S.; vol. 2, Summer 1998; 2 pages.
Lexli Associate Registration; LexLi International, Inc.; 21 pages; Sep. 16, 2005.

* cited by examiner

*Primary Examiner* — Sreeni Padmanabhan
*Assistant Examiner* — Layla Soroush
(74) *Attorney, Agent, or Firm* — Merchant & Gould, P.C.

(57) ABSTRACT

A cosmetic composition is provided including about 25 wt % to about 55 wt % *Aloe vera* gel, about 9 wt % to about 33 wt % exfoliant, about 5 wt % to about 20 wt % vitamin C, and about 0.25 wt % to about 1.0 wt % retinyl propionate (vitamin A), wherein said composition has a pH of about 2.0 to about 3.7. Methods of using said composition are also included.

16 Claims, No Drawings

COSMETIC COMPOSITION AND METHODS OF USE

FIELD OF THE INVENTION

The invention relates to a cosmetic composition and to a method of using a cosmetic composition.

BACKGROUND OF THE INVENTION

The skin is subject to abuse by many extrinsic and environmental factors, as well as coronal aging or intrinsic factors. Common extrinsic factors include ultraviolet radiation, pollutants, trauma and other exogenous agents and radiation. These extrinsic and intrinsic factors lead to wrinkling of skin. To many people, skin wrinkles are a reminder of aging. As a result, elimination of wrinkles has become an important concern in societal thinking.

Treatments for reducing wrinkles range from cosmetic creams and moisturizers to numerous forms of aesthetic surgery. Coronal aging results in the thinning and general degradation of skin. As the skin naturally ages, there is a reduction in the number of skin cells and blood vessels that supply the skin. There is also a flattening of the dermal-epidermal junction which results in weaker mechanical resistance to extraneous forces. As a consequence, aged people are more susceptive to blister formation, mechanical trauma and disease processes.

Combinations of various α-hydroxy acids and humectants have been sold for many years. The use of these products has achieved some cosmetic improvement in wrinkles, skin turgor, and tension of skin.

An exfoliant is more effective at a lower pH. However, too low of a pH can produce burns of the skin. There is an unmet need to provide an exfoliant with a low pH that would not burn a person's skin.

SUMMARY OF THE INVENTION

A cosmetic composition is provided by the invention. Embodiments of the cosmetic composition include about 25 wt % to about 55 wt % *Aloe vera* gel, about 9 wt % to about 33 wt % exfoliant, about 5 wt % to about 20 wt % vitamin C, and about 0.25 wt % to about 1.0 wt % retinyl propionate, wherein said composition has a pH of about 2.0 to about 3.7. Vitamin C is preferably provided as encapsulated vitamin C.

A cosmetic composition may include an exfoliant. An exfoliant can be an enzymatic exfoliant or a mono- or polyhydroxy acid such as an α-hydroxy acid, β-hydroxy acid, or tannic acid. The exfoliant can be glycolic acid, lactic acid, citric acid, salicylic acid, tannic acid, or a mixture thereof.

In an embodiment, the cosmetic composition includes about 25 wt % to about 55 wt % *Aloe vera* gel, about 4 wt % to about 20 wt % α-hydroxy acid, about 2 wt % to about 5 wt % β-hydroxy acid, about 5 wt % to about 20 wt % Vitamin C, about 3 wt % to about 8 wt % gluconolactone, and about 0.25 wt % to about 1.0 wt % retinyl propionate, wherein said composition has a pH of about 2.0 to about 3.7.

In a particular embodiment, the cosmetic composition includes about 25 wt % to about 55 wt % *Aloe vera* gel, about 2 wt % to about 10 wt % glycolic acid, about 2 wt % to about 10 wt % lactic acid, about 2 wt % to about 5 wt % salicyclic acid, about 5 wt % to about 20 wt % Vitamin C, about 3 wt % to about 8 wt % gluconolactone, and about 0.25 wt % to about 1.0 wt % retinyl propionate, wherein said composition has a pH of about 2.0 to about 3.7.

Embodiments of the cosmetic composition can include additional components. Embodiments of the cosmetic composition can include about 0.01 wt % to about 2 wt % vitamin E, and more preferably about 0.05 wt % to about 1 wt % vitamin E. In addition, embodiments of the cosmetic composition can include a buffering agent to buffer the cosmetic composition to a pH of about 2.0 and about 3.7. It should be appreciated that the amount of α-hydroxy acid and buffering agent provided in the cosmetic composition is determined to provide the desired level of buffering at the desired pH. Embodiments of the cosmetic composition can additionally include conventional ingredients commonly found in cosmetic compositions including preservatives, colorants, fragrances, opacifiers, emulsifying agents, stabilizers, and the like.

A method for using a cosmetic composition is also provided. Methods of the invention include a step of applying the cosmetic composition to skin. A cosmetic composition is preferably applied to skin once or twice a day.

DETAILED DESCRIPTION OF THE PREFERRED EMBODIMENT

Embodiments of the present invention provide a cosmetic composition for treating the condition of coronal aging, such as wrinkling and fine lines, leathering, yellowing, sagging, hyperpigmentation and general signs of aging. Embodiments of the cosmetic composition enhance the general tone, glow, and firmness of the skin.

An aspect of the invention includes a cosmetic composition. Embodiments of the cosmetic composition include about 25 wt % to about 55 wt % *Aloe vera* gel, about 9 wt % to about 33 wt % exfoliant, about 5 wt % to about 20 wt % vitamin C, and about 0.25 wt % to about 1.0 wt % retinyl propionate (retinol, an ester of vitamin A), wherein said composition has a pH of about 2.0 to about 3.7. In an embodiment, a cosmetic composition includes exfoliant, wherein the exfoliant includes about 4 wt % to about 20 wt % α-hydroxy acid, about 2 wt % to about 5 wt % β-hydroxy acid, and about 3 wt % to about 8 wt % gluconolactone. In an embodiment, a cosmetic composition includes exfoliant, wherein the exfoliant includes about 2 wt % to about 10 wt % glycolic acid, about 2 wt % to about 10 wt % lactic acid, about 2 wt % to about 5 wt % salicylic acid, and about 3 wt % to about 8 wt % gluconolactone.

In an embodiment, a cosmetic composition preferably includes encapsulated vitamin C. Encapsulated vitamin C can be characterized as beads containing vitamin C. After application of a cosmetic composition to skin, it is believed that the beads dissolve or rupture releasing vitamin C. Until the beads dissolve or rupture, the vitamin C remains isolated from the α-hydroxy acid. Embodiments of the cosmetic composition can optionally include vitamin E, and/or conventional ingredients commonly found in cosmetic compositions including preservatives, colorants, fragrances, opacifiers, emulsifying agents, and stabilizers.

The term "*Aloe vera* gel" refers to a colorless mucilaginous gel obtained from the parenchymatous cells in the fresh leave of an *aloe vera* plant. The *aloe vera* plant belongs to the tree lily (Lillaceae) family. *Aloe vera* is an anti-inflammatory that soothes the skin, reduces itching, and relieves skin irritation. *Aloe vera* gel includes a relatively pure grade of *Aloe vera* gel. Preferably, *Aloe vera* gel is of a quality certified by the International *Aloe* Science Council. *Aloe vera* gel is generally recognized as a wound healing agent and is known to aid in delivery of active ingredients to skin. Embodiments of the cosmetic composition can be considered an *Aloe vera* gel based composition when *Aloe vera* gel is the largest single component of the composition. Preferably, *Aloe vera* gel is provided in an amount that makes it the largest single component in embodiments of the cosmetic composition. In general, it is desirable to provide as much *Aloe vera* gel in a cosmetic composition as possible. Preferably, an amount of *Aloe vera* gel provided in embodiments of the cosmetic composition is about 25 wt % to about 55 wt %, and more preferably about 30 wt % to about 50 wt %, based on the weight of the cosmetic composition. Particularly preferred cosmetic compositions according to the invention include about 48 wt % to about 50 wt % *Aloe vera* gel. It should be understood that the use of the phrase "wt %" refers to the weight percent of a component based on the weight of the cosmetic composition. Additionally, the wt % of the *Aloe vera* gel is of *Aloe vera* gel and not of diluted *Aloe vera* gel.

An exfoliant helps to remove dead or dying skin cells and further improves the skin's own ability to absorb moisture directly from the atmosphere in combination with one or more hydrophilic agents to help absorb moisture from the atmosphere. An exfoliant may be an enzymatic exfoliant, or an acidic exfoliant. Any known enzymatic exfoliant may be used in the compositions and methods of the invention. Examples of enzymatic exfoliants useful in embodiments of the compositions and methods of the invention include, but are not limited to, papain, from papaya, and bromalein, from pineapple.

Examples of acidic exfoliants include, but are not limited to, a mono- or poly-hydroxy acid, tannic acid, or a mixture thereof, or a pharmaceutically acceptable salt or ester thereof. Suitable mono- or poly-hydroxy acids for use in a composition of the invention include alkyl hydroxycarboxylic acids, aralkyl and aryl hydroxycarboxylic acids, polyhydroxy-carboxylic acids, and hydroxy-polycarboxylic acids. Such mono- or poly-hydroxy acids are exemplified by: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl)lactic acid; 3-(4-hydroxyphenyl)lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof, methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof, 4-hydroxyphenyl pyruvic acid and esters thereof, and 2-hydroxyphenyl pyruvic acid and esters thereof.

Poly-hydroxy acidic components can be an α-hydroxy acid that includes, but is not limited to, citric acid, glycolic acid, and lactic acid. In another embodiment a poly-hydroxy acidic exfoliant is a β-hydroxy acid. A preferred β-hydroxy acid is salicylic acid. Poly-hydroxy acidic components can include a mixture of an α-hydroxy acid and a β-hydroxy acid.

The term "pharmaceutically acceptable salt" refers to a salt prepared from a pharmaceutically acceptable non-toxic acid. Examples of suitable inorganic metallic bases for salt formation with acid compounds of the invention include, but are not limited to, aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

An α-hydroxy acid is generally provided in embodiments of the cosmetic composition as a keratolytic agent for assisting in exfoliating skin. There should be a sufficient amount of α-hydroxy acid to provide a cosmetic composition with desired exfoliation properties. In general, a sufficient amount of an α-hydroxy acid should be provided in embodiments of the cosmetic composition to provide a cosmetic composition with a pH of about 3.7 or less. If the pH of a composition is greater than 3.7, the exfoliation property of the composition deteriorates. Preferably, the pH of embodiments of the composition is sufficiently high so that the composition can be made available for home use and sold over the counter. Accordingly, the pH of embodiments of the composition is preferably equal to or greater than about 2.0. When the α-hydroxy acid is provided as a 70% active solution of alpha hydroxy acid, it is preferably provided in the cosmetic composition in an amount of about 15 wt %. In general, an amount of α-hydroxy acid present in a cosmetic composition is sufficient to provide the composition, whether buffered or not buffered, with a pH of about 3.7 to about 2.0. A preferred α-hydroxy acid that can be used according to the invention is glycolic acid. Conventional cosmetic buffering agents can be used in embodiments of the cosmetic composition to provide a cosmetic composition with a pH of about 3.7 to about 2.0. Preferably the composition has a pH of about 3.50 to about 2.0, about 3.0 to about 2.0, about 2.9 to about 2.0, about 2.8 to about 2.0, about 2.75 to about 2.0, about 2.7 to about 2.0, about 2.6 to about 2.0, about 2.5 to about 2.0, about 2.4 to about 2.0, about 2.3 to about 2.0, about 2.25 to about 2.0, about 2.2 to about 2.0, or about 2.1 to about 2.0.

Besides an ability to be an exfoliant, gluconolactone is also a chelating agent that can be used as a moisturizer in compositions applied topically to the skin.

Vitamin C is provided for enhancing skin collagen metabolism and rejuvenation. Accordingly, vitamin C is provided in the cosmetic composition in an amount sufficient to provide the desired level of skin collagen metabolism and rejuvenation, but should not be provided in an amount which causes a reduction of the presence of other beneficial components. Preferably, an amount of vitamin C provided in a cosmetic composition is about 5 wt % to about 20 wt % and, more preferably, about 10 wt % to about 15 wt % for vitamin C having an active level of about 20%. In general, vitamin C is commercially available as an aqueous solution containing 20% ascorbic acid.

Vitamin C tends to oxidize in the presence of an α-hydroxy acid such as glycolic acid. According to an embodiment of the invention, vitamin C can be provided as encapsulated vitamin C in order to reduce oxidation of the vitamin C when provided in a cosmetic composition according to the invention. Encapsulated vitamin C can be referred to as beads. A preferred type of beads containing vitamin C can be referred to as Fluorosome® beads. It is believed that these beads either rupture or dissolve upon application to skin. It is believed that the rubbing of the beads into skin causes a warming of the beads causing them to dissolve or rupture. Once the beads dissolve or rupture, they release vitamin C to the skin.

A cosmetic composition preferably includes retinyl proprionate (retinol, a vitamin A ester) for enhancing exfoliation and collagen activation. Retinyl proprionate is an optional component in embodiments of the cosmetic composition, but, when it is present, it is preferably present at a concentration of about 0.25 wt % to about 1.0 wt %. A preferred cosmetic composition according to the invention includes about 1 wt % retinyl proprionate.

Vitamin E can be added to the cosmetic composition to enhance collagen stimulation and address scar tissue formation. Vitamin E is an optional component of a cosmetic composition according to the invention. If Vitamin E is incorporated into a cosmetic composition, it is preferably provided in an amount of about 0.05 wt % to about 1 wt %. A preferred cosmetic composition according to the invention includes about 0.1 wt % Vitamin E.

A cosmetic composition can include additional ingredients commonly used in cosmetic compositions. Exemplary additional components include preservatives, colorants, fragrances, opacifiers, emulsifiers, and stabilizers.

Preservatives can desirably be incorporated into a cosmetic composition to protect against the growth of potentially harmful microorganisms. Suitable preservatives that can be used include alkyl esters of para-hydroxybenzoics. Other preservatives that can be used include, but are not limited to, hydantoin derivatives, propionate salts, and a variety of quaternary ammonium compounds. Particularly preferred preservatives include phenoxyethanol, methyl paraben, propyl paraben, imidazolidinyl urea, sodium dehydroacetate, and benzyl alcohol. A preservative should be selected while having regard for a use of a composition and possible incompatibilities between the preservatives and other ingredients. Preservatives are generally preferably employed in amounts ranging from 0.01 wt % to 2 wt % of the composition.

A cosmetic composition can optionally include a colorant. Embodiments of the invention can include a colorant such as dyes, which are soluble or dispersible in the composition, pigments, and nacres. Additional color components can be either organic or inorganic. Examples of useful inorganic pigments include iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium dioxide(white), and mixtures thereof. Other useful pigments are pearlants such as mica, bismuth oxychloride, and treated micas, such as titanated micas and lecithin modified micas. Organic pigments can include natural colorants, synthetic monomeric colorants, and polymeric colorants. Examples include phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Polymeric colorants include nylon powder, polyethylene, and polyesters. The polyesters can include linear, thermoplastic, crystalline or amorphous materials produced using one or more diols and one or more dicarboxylic acids copolymerized with colorants. An exemplary list of cosmetically acceptable colorants can be found in the International Cosmetic Ingredient Dictionary and Handbook, 10th Edition, (1997).

A cosmetic composition can also optionally include an opacifier. Examples of opacifiers include, but are not limited to, sodium or magnesium palmitate, sodium or magnesium stearate or hydroxystearate, acyl derivatives containing a fatty chain, such as monostearates or distearates of ethylene glycol or of polyethylene glycol, fatty-chain ethers such as distearyl ether or 1-hexadecyloxyoctadodecanol.

A cosmetic composition can also optionally include a stabilizer. Examples of stabilizers include, but are not limited to, metal salts of fatty acids, such as, for example, magnesium, aluminum and/or zinc stearate or ricinoleate.

A cosmetic composition can also optionally include a stabilizer or antioxidant. Embodiments of the invention can include, but are not limited to, UV stabilizers and antioxidants such as BHT, BHA, benzophenones such as: 2,4-dihydroxybenzophenone, 2,2'-dihydroxy-4-methoxybenzophenone, 2,2'-dihydroxy-4,4"-dimethoxybenzophenone, 2,2'-dihydroxy-4,4'-dimethoxybenzophenone-5-sulphonic acid and its salts, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulphonic acid and its salts, 4-phenylbenzophenone, 2-ethylhexyl-4'-phenylbenzophenone-2-carboxylate, 2-hydroxy-4-n-octyloxybenzophenone and 4-hydroxy-3-benzophenonecarboxylic acid and its salts; benzotriazole derivatives such as 2-(2'-hydroxy-5'-methylphenyl)-2H-benzotriazole, 2-(2'-hydroxy-5'-tert-octylphenyl)-2H-benzotriazole, 2-(2'-hydroxy-3',5'-di-tert-octylphenyl)-2H-benzotriazole, 2-(2'-hydroxy-5'-cumylphenyl)-2H-benzotriazole and 2-(2'-hydroxy-3',5'-di-cumylphenyl)-2H-benzotriazole; disubstituted methane derivatives such as dianisoyl methane, 4-isopropyl dibenzoyl methane, and 4-tert-butyl-4'-methoxy dibenzoyl methane.

A cosmetic composition can also optionally include an emulsifier. An emulsifier acts to uniformly disperse ingredients throughout a composition. Examples of emulsifiers include, but are not limited to, silicone emulsifiers, polyglyceryl fatty acid esters, and fatty acid alcohols.

A cosmetic composition can be prepared by mixing the components together. In general, encapsulated vitamin C is added last to a cosmetic composition, and the cosmetic composition is gently mixed to avoid rupturing the beads.

In an embodiment, the cosmetic composition according to the invention can be applied to skin and massaged gently into the skin. A method can also include administering an embodiment of the cosmetic composition in an amount sufficient to exfoliate at least a portion of the skin. In general, it is expected that embodiments of the cosmetic composition can be applied once or twice a day to particular areas of the skin.

Embodiments of the cosmetic composition can be formulated as a cream, gel, lotion, ointment, tincture, emulsion, foam, or paste.

Embodiments of the cosmetic composition can include a diluent such as water, aqueous alcohol, glycol or other inactive carrier. Embodiments of the cosmetic composition can also include, but not be limited to, a carrier, excipient, or vehicle ingredients such as water, acetone, ethanol, ethylene glycol, propylene glycol, butane-1,3 diol, isopropyl myristate, isopropyl palmitate, mineral oil, and mixtures thereof. Additionally, moisturizers or humectants can be added to embodiments of the cosmetic composition.

The above specification provides a complete description of the manufacture and use of the composition of the invention. Since many embodiments of the invention can be made without departing from the spirit and scope of the invention, the invention resides in the claims hereinafter appended.

EXAMPLES

A cosmetic composition comprising:

| Component | Weight Percent | Percent |
|---|---|---|
| *Aloe vera* gel | 25-55 | 30.0 |
| Glycolic acid | 2.0-10.0 | 3.0 |
| Vitamin C | 5.0-20 | 5.0 |
| Lactic Acid | 2.0-10.0 | 4.0 |
| Salicylic Acid | 2.0-5.0 | 3.0 |
| Gluconolactone | 3.0-8.0 | 5.0 |
| Retinyl Propionate | 0.25-1.0 | 5.0 | wherein in the composition has a pH 2.0-3.7

I claim:

1. A cosmetic composition comprising:
    (a) about 25 wt % to about 55 wt % *Aloe vera* gel;
    (b) an exfoliant comprising a mixture of about 2 wt % to about 10 wt % α-hydroxy acid, selected from glycolic acid or lactic acid about 2 wt % to about 10 wt % of a β-hydroxy acid, salicylic acid and about 3 wt % to about 8 wt % gluconolactone;
    (c) about 5 wt % to about 20 wt % vitamin C; and
    (d) about 0.25 wt % to about 1.0 wt % retinyl propionate;
    wherein the composition has a pH of about 2.0 to 2.25.

2. The cosmetic composition according to claim 1, further comprising about 0.05 wt % to about 1 wt % Vitamin E.

3. The cosmetic composition according to claim 1, further comprising a buffering agent.

4. The cosmetic composition according to claim 1, further comprising a preservative.

5. The cosmetic composition according to claim 1, wherein the vitamin C is provided as encapsulated vitamin C.

6. The cosmetic composition according to claim 1, wherein the *Aloe vera* gel is provided in an amount of about 30 wt % to about 50 wt %.

7. A method for using a cosmetic composition, the method comprising:
    applying a cosmetic composition according to claim 1 to skin.

8. The method according to claim 7, wherein the cosmetic composition further comprises about 0.05 wt % to about 1 wt % Vitamin E.

9. The method according to claim 7, wherein the cosmetic composition further comprises a buffering agent.

10. The method according to claim 7, wherein the cosmetic composition further comprises a preservative.

11. The method according to claim 7, wherein the Vitamin C is provided as encapsulated Vitamin C.

12. The method according to claim 7, wherein the *Aloe vera* gel is provided in an amount of about 30 wt % to about 50 wt %.

13. The cosmetic composition according to claim 1, wherein the exfoliant comprises about 2 wt % to about 5 wt % salicylic acid.

14. A cosmetic composition comprising:
    (a) about 25 wt % to about 55 wt % *Aloe vera* gel;
    (b) an exfoliant comprising a mixture of about 2 wt % to about 10 wt % glycolic acid, about 2 wt % to about 10 wt % salicylic acid, and about 3 wt % to about 8 wt % gluconolactone;
    (c) about 5 wt % to about 20 wt % encapsulated vitamin C;
    (d) about 0.25 wt % to about 1.0 wt % retinyl propionate;
    (e) about 0.05 wt % to about 1 wt % Vitamin E;
    (f) a buffering agent; and
    (g) a preservative;
    wherein the composition has a pH of about 2.0 to 2.25.

15. The cosmetic composition according to claim 1, wherein the composition has a pH of 2.0 to 2.2.

16. The cosmetic composition according to claim 14, wherein the composition has a pH of 2.0 to 2.2.

* * * * *